United States Patent
Lali et al.

(10) Patent No.: US 9,963,725 B2
(45) Date of Patent: May 8, 2018

(54) PROCESS FOR FRACTIONATION OF OLIGOSACCHARIDES FROM AGRI-WASTE

(71) Applicant: Arvind Mallinath Lali, Mumbai (IN)

(72) Inventors: Arvind Mallinath Lali, Mumbai (IN); Annamma Anil Odaneth, Mumbai (IN); Mukesh Prabhakar Pednekar, Mumbai (IN)

(73) Assignee: Arvind Mallinath Lali, Mumbai (IN)

( * ) Notice: Subject to any disclaimer, the term of this patent is extended or adjusted under 35 U.S.C. 154(b) by 14 days.

(21) Appl. No.: 15/112,095

(22) PCT Filed: Jan. 16, 2015

(86) PCT No.: PCT/IB2015/000030
§ 371 (c)(1),
(2) Date: Oct. 13, 2016

(87) PCT Pub. No.: WO2015/107413
PCT Pub. Date: Jul. 23, 2015

(65) Prior Publication Data
US 2016/0340705 A1 Nov. 24, 2016

(30) Foreign Application Priority Data
Jan. 16, 2014 (IN) .......................... 155/MUM/2014

(51) Int. Cl.
| | |
|---|---|
| C08B 37/00 | (2006.01) |
| C12P 21/06 | (2006.01) |
| C12P 19/04 | (2006.01) |
| C08H 8/00 | (2010.01) |
| D21C 5/00 | (2006.01) |
| C12P 19/00 | (2006.01) |
| C12P 19/14 | (2006.01) |

(52) U.S. Cl.
CPC .......... *C12P 19/04* (2013.01); *C08B 37/0057* (2013.01); *C08H 8/00* (2013.01); *C12P 19/00* (2013.01); *C12P 19/14* (2013.01); *D21C 5/005* (2013.01); *C12P 2201/00* (2013.01)

(58) Field of Classification Search
CPC ....... C12P 19/04; C12P 19/14; C12P 2201/00; C12P 21/06; C08B 37/0057; C08B 37/00; D21C 5/005; C08H 8/00
USPC ...................................................... 435/68.1
See application file for complete search history.

(56) References Cited

U.S. PATENT DOCUMENTS

| | | | |
|---|---|---|---|
| 7,947,656 B2 | 5/2011 | Yamasaki et al. | |
| 2008/0032344 A1* | 2/2008 | Fallavollita | C08B 37/0003 435/72 |
| 2009/0053777 A1 | 2/2009 | Hennessey et al. | |
| 2009/0062232 A1 | 3/2009 | Fujikawa et al. | |
| 2010/0021975 A1 | 1/2010 | Sixta et al. | |
| 2010/0255554 A1 | 10/2010 | Benson et al. | |
| 2012/0052534 A1* | 3/2012 | Harlick | C12P 7/10 435/105 |

FOREIGN PATENT DOCUMENTS

| | | | |
|---|---|---|---|
| EP | 0490929 B1 | 1/1996 | |
| EP | 1304412 A2 | 4/2003 | |
| JP | 2008136376 A | 6/2008 | |
| WO | WO-91/03566 A1 | 3/1991 | |
| WO | WO-2006063467 A1 | 6/2006 | |
| WO | WO-2011157427 A1 | 12/2011 | |
| WO | WO2012/021056 A1 * | 2/2012 | ............... C08B 1/08 |
| WO | WO-2013101650 A1 | 7/2013 | |

OTHER PUBLICATIONS

Kuhad et al. Microbial Cellulases and Their Industrial Applications; Enzyme Research, vol. 2011, pp. 1-10.*
Lynd et al, "Microbial Cellulose Utilization: Fundamentals and Biotechnology," *Microbiology and Molecular Biiology Reviews*, vol. 66, No. 3 Sep. 2002, pp. 506-577.
Moreira et al., "The Hydrolysis of Agro-Industrial Residues by Holocellulose-Degrading Enzyme," *Brazilian Journal of Microbiology*, pp. 498-505 (2012).
Peng et al., "Fractional purification and bioconversion of hemicelluloses," *Biotechnology Advances*, 30 pp. 879-903 (2012).

(Continued)

*Primary Examiner* — Scott Long
*Assistant Examiner* — Paul C Martin
(74) *Attorney, Agent, or Firm* — Marshall, Gerstein & Borun LLP

(57) ABSTRACT

The present invention provides a continuous and cost effective chemo-enzymatic process for fractionation of holocellulose, obtained from agri-waste, into arabinoxylooligosaccharides, xylooligosaccharides and cellooligosaccharides, suitable for commercial applications. The process comprises of mixing the holocellulose with an aqueous medium in a controlled condition to obtain an aqueous extract comprising of soluble arabinoxylooligosaccharides and insoluble solid fraction; followed by treatment of the solid fraction with an aqueous alkali solution at controlled condition to obtain soluble xylooligosaccharides and cellulose residue. The cellulose residue is thereafter suspended in aqueous acid solution followed by treatment with an enzyme at controlled condition to obtain soluble cellooligosaccharides. The arabinoxylooligosaccharides, xylooligosaccharides and cellooligosaccharides obtained from the process have a degree of polymerization greater than 4.

16 Claims, 1 Drawing Sheet

(56) References Cited

OTHER PUBLICATIONS

M. Alger "Polymer Science Dictionary Third Edition" © 2017, Springer Netherlands, p. 371. (2017).
Boonwong et al., "Agricultural Wastes Potential (Pineapple Crown, Durian Peel and Sugarcane Leaves) on Reducing Sugar Production by Using Sulfuric Acid Pretreatment Following Enzymatic Hydrolysis," *KKU Res. J.*, pp. 361-369 (2014).

\* cited by examiner

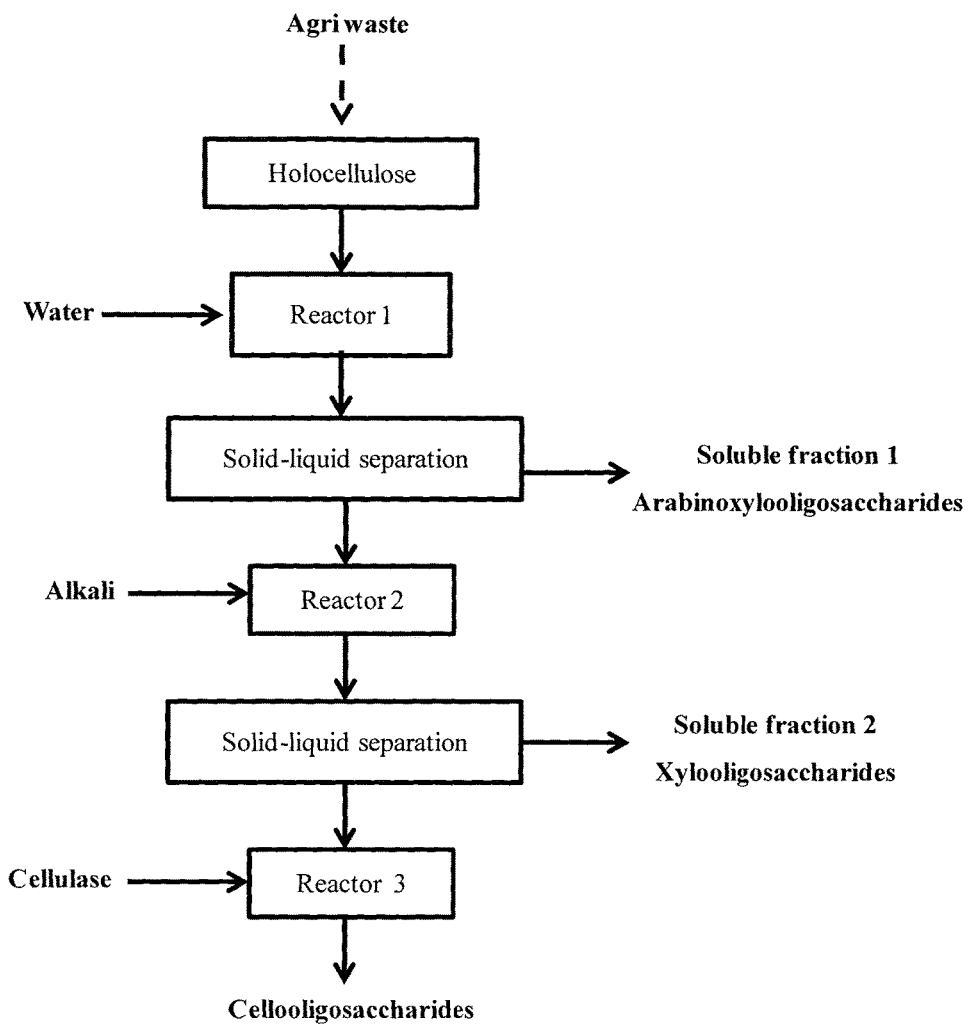

PROCESS FOR FRACTIONATION OF OLIGOSACCHARIDES FROM AGRI-WASTE

FIELD OF INVENTION

The present invention relates to a continuous, efficient and inexpensive chemo-enzymatic sequential process for fractionation of oligosaccharides into arabinoxylooligosaccharides, xylooligosaccharides and cellooligosaccharides, suitable for commercial applications, from agri waste.

BACKGROUND OF INVENTION

Oligosaccharides form an important group of polymeric carbohydrate that is extensively used as food additives and nutritional supplements. Oligosaccharides are composed of monomeric sugar units linked by glycosidic bond with a degree of polymerization 2 to 10. They are hydrolyzed readily by acid or enzyme to their respective monomeric sugar constituents. Oligosaccharides provide several health benefits which make them useful as food additives. Physiochemical and physiological property of the oligosaccharide vary depending on the mixture of oligosaccharide produced. Oligosaccharides having degree of polymerization 3 to 10 are prebiotic, with low colorific value, and are used as soluble dietary fiber.

Oligosaccharides are produced either by non-enzymatic methods or enzymatic methods. Non-enzymatic methods involve extraction of oligosaccharides from natural source and chemical synthesis using monosaccharides or disaccharides as starting material. Enzymatic methods involve synthesis of oligosaccharides using glycosidases and glycotransferases as catalyst and enzymatic hydrolysis of polysaccharides into oligosaccharides.

Production of oligosaccharides from agri-waste leads to exploitation of agri-waste, such as shell, bran, husk, hull, cob and oilseed meal, which is otherwise used as animal feed. These wastes contain majorly of cellulose and hemicellulose along with proteins, phytochemicals and lignin. All these constituents are arranged in a complex polymeric matrix which prevents accessibility of polysaccharides for hydrolysis. However, thermo-chemical treatment provides amenable biomass which when further subjected to controlled enzymatic hydrolysis helps to achieve a high yield of oligosaccharides of desired properties. Production of bioactive oligosaccharides from easily available agri-waste gives promising benefits to agro-based industry.

The prior arts provide various methods for manufacture of oligosaccharides from biomass. These methods involve the use of either microbial cell or enzymes for breakdown of biomass into oligosaccharides. However, the methods described in the prior art require specific enzymes for production of oligosaccharides. The methods described in the prior art produce mixture of oligosaccharide which require downstream operations for its purification, thereby increasing the cost of production.

U.S. Pat. No. 5,246,840 discloses a method for synthesis of oligosaccharides by using glycosidases and glycotransferases as catalysts. Oligosaccharide synthesis was achieved by combining glycosidase catalyzed synthesis of shorter oligosaccharides with glycotransferase catalyzed synthesis of higher oligosaccharides.

U.S. Pat. No. 4,677,198 discloses a process for the preparation of oligosaccharides-containing products from biomass, which provides use of hydrochloric acid for partial hydrolysis of biomass to easily fermentable oligosaccharides containing products and easy recovery of acid. These oligosaccharides were further subjected to fermentation for preparation of products like ethanol.

JP2008136376 describes a process for production of acidic xylooligosaccharides, from wheat/rice bran. In this process, acidic xylooligosaccharides was obtained after hot water treatment, under acidic condition of pH range of 1.0-4.0, or under alkaline condition of pH range of 9.0-13.0 of wheat bran or rice bran at temperature in between 100-150° C. followed by ion exchange treatment. The process yields acidic xylooligosaccharides, having degree of polymerization 2-5.

EP1304412 discloses a method for production of xylooligosaccharides from lignocellulosic pulp using enzymes, which comprises enzymatic hydrolysis of lignocellulose pulp using hemicellulases followed by membrane separation to obtain non permeate fraction with high concentration of xylooligosaccharides-lignin mixture which was further treated to recover xylooligosaccharides.

U.S. Pat. No. 4,908,311 discloses a method for cellooligosaccharide from cellulose-base substance by enzymes. Cellulase produced by microorganism belonging to the Genus *Cellvibrio* was used as catalyst for enzymatic break down of cellulose material. Enzymatic hydrolysis in combination with membrane filtration reactor helps in removal of inhibitors and accumulation of cellooligosaccharides.

U.S. Pat. No. 7,947,656 describe a process for production of cellooligosaccharides by enzymatically decomposing a cellulose material. The process consisting of breakdown of cellulosic material, having an average degree of polymerization not greater than 700 and average particle size not greater than 100, using cellulase to selectively produce cellooligosaccharides.

US20110020498 discloses a process for preparation of (arabino) xylan oligosaccharides from wheat bran using endoxylanase. Further process includes destarching, deproteination followed by enzyme hydrolysis with endoxylanase from *Bacillus subtilis*. The purification of (arabino) xylan oligosaccharide was done with ion exchange chromatography. This process was produced (arabino) xylan oligosaccharides with average degree of polymerization between 4 and 10 with average degree of arabinose substitution between 0.15 and 0.35 and has good organoleptic and color properties.

US20100021975 describes a process for production of xylooligosaccharides by cold caustic extraction of pulp obtained after cooking process. The process involves cold caustic extraction of xylan followed by membrane separation process to obtain xylan enrich retentate. This xylan fraction is further processed by hydro-thermolysis and enzymatic hydrolysis for conversion of xylan into xylooligosaccharides.

US20090062232 describes method for preparation of high purity xylooligosaccharides from plant material comprising of alkali treatment, pressure and heat treatment of plant material followed by solid-liquid separation. Solid residue was further subjected to enzyme hydrolysis using xylanases. Crude saccharide extract was concentrated followed by the desalting and active carbon treatment to produce high purity xylooligosaccharides composition free from UV absorbing substances and coloring impurities.

US20110244073 describes a method for preparation of arabinoxylan and arabinoxylo-oligosaccharides. The process for preparation of water soluble arabinoxylan includes hot water treatment of water-unextracted arabinoxylan in the presence of thermostable amylase followed by addition of ethanol to final concentration of 70/30 (v/v) ethanol/water after cooling to 70° C.

U.S. Pat. No. 5,633,032 describes a method for preparation of cereal extracts. In this process cereal bran material obtained from milling was subjected to alkali treatment at temperature 70-80° C. followed by solid-liquid separation. Insoluble residue was again treated with alkaline hydrogen peroxide at 70-80° C. followed by solid-liquid separation. Soluble fraction was then spray dried and used as adhesive and thickening agent.

US20120231147 relates to the production of xylooligosaccharides by auto-hydrolysis of grain products. In this process corn fiber separated was from distillers and the dried grains with solubles (DDGS) was subjected to auto-hydrolysis using deionized water at temperature in the range of 140-220° C. to give an extract containing xylooligosaccharides, monosaccharides and acid. This extract was further hydrolyzed using acid to form monosaccharides.

US20120232264 describes a two-step process for biomass treatment. The first step of process involves treatment of biomass with pressurized water at a temperature between 100 to 200° C. to release hemicellulose as xylooligosaccharides. In the second step, insoluble residue was again treated with pressurized water at a temperature of 200 to 300° C. to obtain cellooligosaccharides. Thus the obtained xylooligosaccharides and cellooligosaccharides were further hydrolyzed using solid acid catalyst to generate xylose and glucose respectively.

US20120115192 provides a process of production of fermentable sugars from biomass using multi-step multi-enzyme system. In this process, biomass was first treated with 5% to 10% w/v alkali at temperature ranging from 50 to 200° C. under 1 to 20 bar pressure for removal of hemicellulose leaving behind cellulose residue. Furthermore hemicellulose was precipitate by addition of ethanol solvent. Thus, precipitated hemicellulose and cellulose were then enzymatically hydrolyzed using xylanases and cellulases preparation for production of fermentable sugars.

The above described methods produce either xylooligosaccharides or cellooligosaccharides from biomass using enzymatic and chemical methods. Enzymatic methods involve treatment of biomass with cell-wall modifying enzymes such as amylase, glucoamylase, protease, pullunase and lipase for removal of starch and non-carbohydrate components. Thereafter, the carbohydrate contained in the biomass is hydrolyzed using either xylanase or cellulase to produce xylooligosaccharides or cellooligosaccharides respectively. The two step process described in the prior art increases the overall cost of production as it requires chemical pretreatments for polysaccharide extraction followed by its hydrolysis into oligosaccharides using specific enzymes.

SUMMARY OF THE INVENTION

The present invention relates to a process for fractionation of oligosaccharides, wherein the process comprises of subjecting the holocellulose, produced from agri-waste, with an aqueous medium at controlled conditions to obtain an aqueous extract comprising of soluble arabinoxylooligosaccharides and insoluble solid fraction. The insoluble solid fraction, recovered from the aqueous extract, is thereafter mixed with alkaline solution of molar concentration in between 0.2-2.5M, at a temperature ranging from 100-150° C. in reactor for 20-40 mins to obtain hemicellulose extract. The hemicellulose extract is filtered to obtain xylooligosaccharides as filtrate and cellulose as residue. The cellulose residue is treated with an enzyme solution of pH 5.0 for 2 hrs, to hydrolyze the cellulose into cellooligosaccharides.

One object of present invention is to provide a process for obtaining soluble arabinoxylooligosaccharides, soluble xylooligosaccharides and soluble cellooligosaccharides having a degree of polymerization greater than 4.

The present invention provides for a process for fractionation of oligosaccharides from agri-waste wherein the process comprises of treating the holocellulose, obtained from agri-waste, with water at a temperature ranging from 100 to 140° C. for 30 mins, to obtain aqueous extract containing arabinoxylooligosaccharides.

Another object of the present invention is to provide a process for production of xylooligosaccharides from water insoluble solid fraction using thermo-alkaline process devoid of enzymes such as arabinoxylanases and xylanases.

One of the objects of the present invention is to produce soluble cellooligosaccharides having degree of polymerization greater than 4, by controlled enzymatic hydrolysis of cellulose residue.

Thus the present invention provides for stepwise treatment of holocellulose, obtained from agri waste, with water, alkali and enzyme to yield separate product streams containing soluble arabinoxylooligosaccharides, xylooligosaccharides and cellooligosaccharides respectively. The present invention is cost effective since all the chemical extractions are carried out at milder conditions. The prevent invention also does away with the requirement of additional step for purification of oligosaccharides as the process generates separate product streams containing different oligosaccharides.

BRIEF DESCRIPTION OF THE DRAWINGS

The invention will be described further with respect to the following in which:

FIG. 1 provides for a schematic depiction of production of oligosaccharide from holocellulose, prepared from agri-waste. The holocellulose is treated with water at a temperature between 100 to 140° C. in reactor 1 for 20-40 mins to form an aqueous extract. The aqueous extract is then subjected to solid-liquid separation to produce soluble fraction 1, containing arabinoxylooligosaccharides, and insoluble solid fraction. The insoluble solid fraction, obtained from reactor 1, is subjected to alkali solution of molar concentration ranging between 0.2-2.5M at a temperature between 100-150° C. in reactor 2; followed by solid-liquid separation to obtain soluble fraction 2, containing xylooligosaccharides, and insoluble residue of cellulosic nature. The cellulose residue is subjected to controlled enzyme hydrolysis, in acidified water of pH 5.0 and at a temperature in the range of 45-55° C. in Reactor 3 for 2 hrs for cellooligosaccharide production.

DETAILED DESCRIPTION OF THE INVENTION

Definitions

The term "holocellulose" used herein refers to carbohydrate fraction obtained from alkali pretreatment of lignocellulosic material that includes cellulose, a common building block made of sugar (glucose) that is the most abundant biopolymer, as well as hemicellulose.

The term "aqueous extract" used herein refers to the extract obtained by a process of mixing the holocellulose with an aqueous medium at controlled conditions.

The term "insoluble solid fraction" used herein refers to the fraction obtained by the filtration of the aqueous extract.

The term "hemicellulose extract" used herein refers to the extract obtained by the process of extraction in which insoluble solid fraction is treated with the alkaline solution.

The present invention relates to fractionation process for oligosaccharides from agri-waste. It also provides step wise chemo-enzymatic treatments of holocellulose, obtained from agri-waste, to produce arabinoxylooligosaccharides, xylooligosaccharides and cellooligosaccharides in separate product streams that can be further transformed into products of commercial applicability. The described process gives high efficiency in terms of time for the production of oligosaccharides. The mild reaction condition and better utilization of enzymes makes the present invention to be economically more beneficial than the methods described in the prior art.

The present invention provides a process for fractionation of oligosaccharide from agri-waste at controlled condition such as temperature, pH, time of contact and other parameters to achieve step-wise fractionated oligosaccharide.

Another object of the invention is to provide stepwise treatment of holocellulose to give separate product streams containing soluble arabinoxylooligosaccharides, xylooligosaccharides and cellooligosaccharides.

Another objective of the present invention is to provide cost effective process having milder conditions without the need of purification processes to obtain the desired product.

Yet another objective of the present invention is to provide much cleaner and low energy-consuming process for hemicellulose and cellulose hydrolysis, resulting in fractionation of oligosaccharide with better quality and high yield.

In accordance of the present invention, arabinoxylooligosaccharides can be obtained from holocellulose using water treatment. In an embodiment of the present invention, the solid-liquid ratio of holocellulose with water is in the ratio of 1:10 (w/v) to make the slurry. Thereafter the slurry is subjected to hydrolysis at controlled conditions.

In an embodiment of the present invention, hydrolysis of holocellulose can be carried out at temperature in the range of 100-140° C. for 20-40 mins, preferably 30 min to obtain aqueous extract. The solid-liquid separation is carried out to recover soluble fraction containing arabinoxylooligosaccharides from aqueous extract leaving behind solid fraction.

In accordance of the present invention the process for isolation of xylooligosaccharides comprises of thermo-alkaline treatment of solid fraction, obtained from water treatment, followed by solid-liquid separation to yield hemicellulose extract containing xylooligosaccharides.

One of the embodiment of the present invention provides a process for obtaining hemicellulose extract, wherein process comprises of treating/mixing the solid fraction, obtained from aqueous extract, with alkali solution, having concentration in between 0.2-2.5M at temperature ranging from 100-150° C. in the reactor for 20-40 mins, preferably for 30 mins.

In an embodiment of present invention, the alkali is selected from group consisting of NaOH, KOH, $H_2O_2$, and LiOH.

In accordance with the present invention, the process for fractionation of oligosaccharides from agri-waste, comprises of separating insoluble cellulose from soluble hemicellulosic extract by filtration. Thereafter the insoluble cellulose residue is suspended in water and the pH of the slurry is adjusted to 4.5-5.5 using acid.

In another embodiment of invention, the acidic pH of cellulose slurry is adjusted by using acid, wherein the said acid is selected from a group consisting of $H_2SO_4$, $HNO_3$, HCl, and $CH_3COOH$.

In accordance of the present invention hydrolysis of cellulose, obtained after the thermo-alkaline treatment of insoluble solid fraction, is carried out by using an enzyme under controlled conditions.

In an embodiment of the present invention the enzyme used for cellulose hydrolysis is selected from group consisting of endo-glucanases, endo-xylanases, mannanases, and galactanases, preferably endo-glucanases.

In yet another embodiment of the present invention, the endo-glucanases is used in the process at a concentration ranging from 10-100 FPU/gm of cellulose, preferably 40.

In the most preferred embodiment of the present invention, the enzyme hydrolysis of cellulose can be carried out at temperature in the range of 45-55° C., and at pH in the range of 4.5-5.5 for 2 hrs followed by filtration, for the conversion of cellulose to cellooligosaccharides. The cellulose residue is dried at a temperature in the range of 40-60° C.

The present invention allows the oligosaccharides to be isolated in substantially pure form from other biomass components. Another advantage of the present invention is that it can be utilized to produce macromolecular polysaccharides with well defined molecular weight distributions and known characteristics, such as water or alkaline solubility. Oligosaccharide produced by the process of the present invention can be utilized as food, feed, pharmaceutical or polymer components. The use of mild thermo-chemical method for the isolation of arabinoxylans ensures that moieties of higher molecular sizes are isolated intact from the agri-waste materials. The present invention enables the production of soluble arabinoxylooligosaccharides, soluble xylooligosaccharides and soluble cellooligosaccharides having a degree of polymerization greater than 4. The operating costs of the process are also low as no pure enzyme preparations (arabinoxylanases, endo-xylanases) are needed for the production of arabinoxylooligosaccharides and xylooligosaccharides. The current production scheme ensures a multi-product recovery from the holocellulose and thereby increasing the overall economic value of the agri-waste. A combination of methods aimed at to valorize phenolics and the other components of the agri-waste can be of great commercial value to the agriculture processing industry.

Following examples are given by the way of illustration of the present invention and not intended to limit the scope of the present invention.

Examples (1) Preparation of Arabinoxylooligosaccharides

Holocellulose, obtained from agri-waste, 100 g was weighed and mixed with water in the ratio 1:10. The slurry was loaded into the reactor and hydrolysis was carried out at temperature 120° C. for 30 mins. The aqueous extract was then subjected to solid-liquid separation using nylon mesh to obtain arabinoxylooligosaccharides filtrate and insoluble solid fraction. The filtrate was further subjected to solvent precipitation to obtain pure arabinoxylooligosaccharides. The insoluble solid fraction was dried at 50° C. Weight of insoluble solid fraction: 53 g, weight of arabinoxylooligosaccharides: 40 g.

TABLE 1

Effect of time on arabinoxylooligosaccharides extraction
with solid to liquid ratio 1:25

| Time (mins) | Arabinoxylooligosaccharide extraction (% w/w of arabinoxylan in holocellulose) |
| --- | --- |
| 20 | 45.31 |
| 30 | 65.44 |
| 45 | 60.41 |

TABLE 2

Effect of temperature on arabinoxylooligosaccharides
extraction with solid to liquid ratio 1:10

| Temperature (° C.) | Arabinoxylooligosaccharides extraction (% w/w of arabinoxylan in holocellulose) |
| --- | --- |
| 100 | 82 |
| 120 | 84 |
| 140 | 81 |

(2) Preparation of Xylooligosaccharides

Insoluble solid fraction; 50 g was treated with sodium hydroxide solution, 0.5 M, in the ratio 1:10 at 120° C. for 30 mins to obtain hemicellulose extract. Hemicellulosic extract was then filtered through nylon cloth to separate xylooligosaccharides and insoluble cellulose residue. Pure xylooligosaccharides was recovered by solvent precipitation. Weight of xylooligosaccharides: 18 gms; Weight of residue: 25 g.

TABLE 3

Effect of alkali concentration on xylooligosaccharide extraction
with solid to liquid ratio 1:10

| Alkali concentration, (M) | Xylooligosaccharide extraction (% w/w of xylan in Insoluble solid fraction) |
| --- | --- |
| 0.25 | 60 |
| 0.5 | 78 |
| 1.25 | 75 |
| 2.5 | 76 |

TABLE 4

Effect of temperature on xylooligosaccharide extraction
with solid to liquid ratio 1:10

| Temperature, (° C.) | Xylooligosaccharide extraction (% w/w of xylan in Insoluble solid fraction) |
| --- | --- |
| 80 | 42 |
| 100 | 62 |
| 120 | 77 |
| 150 | 45 |

TABLE 5

Effect of time on xylooligosaccharide extraction
with solid to liquid ratio 1:10

| Time (mins) | Xylooligosaccharide extraction (% w/w of xylan in Insoluble solid fraction) |
| --- | --- |
| 20 | 58 |
| 30 | 80 |
| 40 | 82 |

(3) Preparation of Cellooligosaccharides

Insoluble cellulose residue, 10 g, was mixed with water in the ratio 1:10 to make the cellulose slurry and the pH of the slurry was adjusted to pH 4.8 by adding HCl. Cellulase, 40 FPU/gm of cellulose, was solubilized in acidified water and then added into the cellulose slurry. Enzyme hydrolysis was performed at 50° C. for 2 hrs. Enzyme hydrolysate containing cellooligosaccharides was then separated by filtration. Weight of cellooligosaccharides: 2.6 g

TABLE 6

Effect of enzyme concentration on cellooligosaccharide extraction

| Enzyme activity, FPU/gm cellulose | Cellooligosaccharide (DP >4) extraction (% w/w of carbohydrates in cellulose) |
| --- | --- |
| 10 | 23 |
| 20 | 28 |
| 40 | 32 |
| 100 | 25 |

We claim:

1. A sequential process for fractionation of different oligosaccharides from holocellulose comprising of:
   a) mixing holocellulose with an aqueous medium at a temperature ranging from 100-140° C. for 20-40 min, to obtain an aqueous extract containing soluble arabinoxylooligosaccharides and an insoluble solid fraction;
   b) treating the solid fraction obtained from step (a) with an aqueous alkali solution, at a temperature in the range of 100-150° C. for 20-40 mins to obtain hemicellulose extract comprising soluble xylooligosaccharides and cellulose residue;
   c) suspending the cellulose residue obtained from step (b) in aqueous acid solution to obtain a cellulose slurry; and
   d) treating the cellulose slurry obtained from step (c) with an enzyme at a controlled temperature in the range of 45-55° C. for the period of 2 hrs to obtain cellulose extract containing soluble cellooligosaccharides.

2. The process as claimed in claim 1, wherein the said holocellulose is obtained from agri-waste comprising shell, bran, husks, hull, cob and oilseed meal.

3. The process as claimed in claim 1, wherein the holocellulose is mixed with the aqueous medium in the ratio of 1:10 at 120° C.

4. The process as claimed in claim 3, wherein the said alkali solution has concentration in the range of 0.2M-2.5M.

5. The process of claim 4, wherein the alkali solution has a concentration of 0.5 M.

6. The process as claimed in claim 1, wherein the said hemicellulose extract is obtained by treating the solid fraction with alkaline solution at 120° C.

7. The process as claimed in claim 1, wherein the said alkali solution has concentration in the range of 0.2M-2.5M.

8. The process of claim 7, wherein the alkali solution has a concentration of 0.5 M.

9. The process as claimed in claim 1, wherein the ratio of cellulose with water to make the cellulose slurry is 1:10 (w/v).

10. The process as claimed in claim 1, wherein the said enzyme is selected from a group consisting of endo-glucanases, endo-xylanases, mannanases, and galactanases.

11. The process as claimed in claim 9, wherein the enzyme is endo-glucanase and said endo-glucanase used in the process is of a concentration in the range of 10 to 100 FPU/gm of cellulose.

12. The process of claim 11, wherein the endo-glucanase concentration is 40 FPU/gm of cellulose.

13. The process of claim 10, wherein the enzyme is endo-glucanase.

14. The process as claimed in claim 1, wherein the soluble arabinoxylooligosaccharides, soluble xylooligosaccharides and soluble cellooligosaccharides obtained by the process have a degree of polymerization greater than 4.

15. The process of claim 1, wherein the mixing of step (a) is performed for 30 min.

16. The process of claim 1, wherein the treatment of step (b) is performed for 30 min.

* * * * *